United States Patent [19]

Vu et al.

[11] Patent Number: 5,384,117
[45] Date of Patent: Jan. 24, 1995

[54] ANTIPERSPIRANT

[75] Inventors: Tuan M. Vu, Brighton, Mass.; Thomas J. Krafton, South Hampton, N.H.; Alan M. Phipps, Framingham, both of Mass.

[73] Assignee: The Gillette Company, Boston, Mass.

[21] Appl. No.: 974,673

[22] Filed: Nov. 12, 1992

Related U.S. Application Data

[63] Continuation of Ser. No. 510,019, Apr. 17, 1990, abandoned, which is a continuation-in-part of Ser. No. 347,073, May 3, 1989, abandoned.

[51] Int. Cl.$^6$ .................. A61K 7/32; A61K 7/34; A61K 7/38
[52] U.S. Cl. .................. 424/66; 424/59; 424/68; 424/401; 514/944
[58] Field of Search .................. 424/66, 68

[56] References Cited

U.S. PATENT DOCUMENTS

| | | | |
|---|---|---|---|
| 3,968,203 | 7/1976 | Spitzer | 424/68 |
| 4,036,949 | 7/1977 | Colodney | 424/49 |
| 4,065,564 | 12/1977 | Miles, Jr. | 424/65 |
| 4,120,948 | 10/1978 | Shelton | 424/66 |
| 4,202,879 | 5/1980 | Shelton | 424/66 |
| 4,346,079 | 8/1982 | Roehl | 424/65 |
| 4,518,582 | 5/1985 | Schamper et al. | 424/66 |
| 4,617,185 | 10/1986 | DiPietro | 424/65 |
| 4,659,564 | 4/1987 | Cox et al. | 424/68 |
| 4,673,570 | 6/1987 | Soldati | 424/66 |
| 4,708,863 | 11/1987 | Bews et al. | 424/47 |
| 4,777,035 | 10/1988 | Shin | 424/68 |
| 4,781,917 | 11/1988 | Luebbe et al. | 424/65 |
| 4,816,261 | 3/1989 | Luebbe et al. | 424/68 |
| 4,859,446 | 8/1989 | Arbutyn et al. | 424/DIG. 5 |
| 4,954,333 | 9/1990 | Ward | 424/68 |
| 4,985,238 | 1/1991 | Tanner et al. | 424/68 |

FOREIGN PATENT DOCUMENTS

| | | | |
|---|---|---|---|
| 0135315 | 3/1985 | European Pat. Off. | 424/68 |
| 291334 | 11/1988 | European Pat. Off. | 424/68 |
| 2430897 | 6/1974 | Germany | 424/68 |

OTHER PUBLICATIONS

Dow Corning, "Information About Cosmetic Ingredients", (1982).
"Deodorant & Antiperspirant Formulary", *Cosmetics and Toiletries*, vol. 100, pp. 65–75 (Dec. 1985).
Dow Corning, "Dow Corning Transparent Antiperspirant Gel Formulation 7635-113A".

*Primary Examiner*—Dale R. Ore
*Attorney, Agent, or Firm*—Stephan P. Williams

[57] ABSTRACT

A substantially clear, anhydrous suspension-type antiperspirant product includes an effective amount of an active antiperspirant component in particulate form suspended in an anhydrous vehicle such that there is no significant dissolution of the active antiperspirant ingredient in the vehicle, and the refractive indices of the active antiperspirant component and the vehicle are matched.

24 Claims, No Drawings

ANTIPERSPIRANT

This is a continuation of application Ser. No. 07/510,019, filed Apr. 17, 1990, now abandoned, which is a continuation-in-part of U.S. Ser. No. 07/347,073, filed May 3, 1989, now abandoned.

The invention relates to antiperspirant products and processes for forming antiperspirant products.

Antiperspirant products are well-known in the cosmetic art. Such antiperspirant products often contain an active antiperspirant ingredient, e.g., aluminum chlorohydrate and a liquid vehicle. Such an active antiperspirant ingredient is soluble in water and water-based antiperspirant products tend to have objectionable characteristics of wetness and tackiness. A gelling agent may be used to provide the antiperspirant product with a solid character. Antiperspirant products of the solid-type are typically used by rubbing an area of the body such as the underarm to apply a layer of the antiperspirant to the skin, which reduces perspiration. It is desirable that antiperspirant products have aesthetic characteristics of smoothness, non-oiliness and non-tackiness. Other desirable characteristics include clarity of the antiperspirant product and the absence of any readily visible residue as, e.g., a white layer, on the skin after the antiperspirant is applied.

In accordance with one aspect of the invention, there is provided a substantially clear, essentially anhydrous suspension-type antiperspirant product that includes an effective amount of an active antiperspirant component in particulate form suspended in an anhydrous vehicle such that there is no significant dissolution of the active antiperspirant ingredient in the vehicle and the refractive indices of the active antiperspirant component and the vehicle are substantially matched. While particular antiperspirant products include a sufficient quantity of a gelling agent so that the antiperspirant product can be used as a solid, a reduced amount of, or no, gelling agent may be used if it is desirable to make a more liquid type product.

A substantially clear antiperspirant product is one that is visually clear, with a minimal amount of haziness or cloudiness. A transparent antiperspirant solid, like glass, allows ready viewing of objects behind it. By contrast, a translucent antiperspirant solid, although allowing light to pass through, causes the light to be so scattered that it will be impossible to see clearly objects behind the translucent solid. In general, an acceptable translucent to clear antiperspirant product has a turbidity measurement expressed in Nephelometric (or Formazin) Turbidity Units in the range of between about 200 and about 800 FTU, and an antiperspirant product is substantially clear if its relative turbidity measurement is less than 400 FTU. Turbidity measurements discussed hereinafter were made with a Hellige #965 Direct-Reading Turbidimeter. Distilled water has a turbidity of 0 FTU and whole milk diluted one part in 350 parts of distilled water has a turbidity of about 200 FTU.

In accordance with another aspect of the invention, the active antiperspirant component is processed prior to incorporation in the antiperspirant product by gentle removal of water without the formation of opacifying contaminants such as aluminum oxide. For example, if the active antiperspirant component contains a contaminant such as aluminum oxide, an insufficiently clear antiperspirant product can result. In one particular method of processing aluminum chlorohydrate without generating opacifying contaminants for use as the active antiperspirant component, water is removed from an aqueous solution of aluminum chlorohydrate by drying the aqueous solution of aluminum chlorohydrate at a temperature less than 40° C., more preferably less than 30° C. The drying preferably is carried out at atmospheric pressure. The resulting glass-like product is then ground into fine (impalpable) particles (typically less than about one hundred microns in size) for use in the antiperspirant product.

In another particular method, a container is charged with an aluminum chlorohydrate (ACH) solution such as ACH-303 or Rehydrol II, and a surfactant, such as Oleth-10 or Procetyl AWS (PPG-5-Ceteth-20), is added. The resulting mixture is then agitated to make a clear solution. Ethanol may be added to facilitate dissolution of the surfactant. Solvent (water) or solvents (water and ethanol) are than removed under vacuum (p>10 mmHg) and elevated temperature (T<50° C.). Removal of solvent or solvents continues until the mass of the dried solid indicates a predetermined (by calculation) quantity of solvent or solvents has been removed. The dried solid ACH/surfactant adduct is stored in a sealed container.

Preferred active antiperspirant components for use in the antiperspirant products are halohydrates (chlorides, bromides, iodides) and include well-known aluminum chlorohydrates, aluminum-zirconium chlorohyrates, and polyhydroxy complexes of basic aluminum salts, such as are commercially-available as Dow Corning ACH-303 or Rehydrol II (supplied by Reheis Chemical Co.). Further examples of active antiperspirant ingredients that have application to this technology include aluminum sesquichlorohydrate, aluminum dichlorohydrate, aluminum chloride, aluminum zirconium trichlorohydrate, aluminum zirconium tetrachlorohydrate, aluminum zirconium pentachlorohydrate and aluminum zirconium octachlorohydrate.

The refractive index of the hydrated active ingredient is a function of the amount of associated water in the solid particulate active ingredient. For example, tray-dried aluminum chlorohydrate has a refractive index $\eta_D$ of about 1.51, and the refractive index of less dried aluminum chlorohydrate (alone or in adduct form) can vary to as low as about 1.46 depending upon the dryness (the amount of water associated with the hydrated salt or adduct). Another useful active ingredient is aluminum-zirconium chlorohydrate that has been dried to have a refractive index $\eta_D$ of about 1.56. The amount of associated water in the solid particulate active ingredient may be adjusted in various ways, including, for example, by controlled drying, by storage of the dried active ingredient in a high humidity atmosphere, or by addition of water to the adduct before addition of a gelling agent.

The active antiperspirant component(s) should be present in an amount effective to reduce perspiration when applied to the skin. The precise limits on the amount of active antiperspirant component that can be used will vary with the particular component and formula. As a general rule, however, the antiperspirant product should contain anywhere from about 5% to about 50% (more preferably about 10% to about 30%) of active antiperspirant component in solid particulate form.

To provide a substantially clear antiperspirant product, the refractive index ($\eta_D$) of the vehicle should be matched to that of the active antiperspirant component. The vehicle generally is a blend of liquids having different refractive indexes. Liquids suitable for use include octylmethoxy cinnamate ($\eta_D$ 1.54), isopropyl myristate ($\eta_D$ 1.43), polyphenylmethylsiloxane liquids such as Dow Corning DC-556 ($\eta_D$ 1.46), isoeicosane (Permethyl 102A) fluid ($\eta_D$ 1.44), cinnamic aldehyde ($\eta_D$ 1.62), SD-40 alcohol ($\eta_D$ 1.36), $C_{12-15}$ alcohols benzoate (Finsolv TN) ($\eta_D$ 1.48), isoamyl methoxy cinnamate ($\eta_D$ 1.56), and isopropyl palmitate ($\eta_D$ 1.48). The vehicle can also include a surfactant, such as Oleth-10 or PPG-5 Ceteth-20 which helps provide washability, provided it is compatible with other requirements of the system. The vehicle can also contain additional cosmetic ingredients such as emollients, colorants, fragrances, and preservatives, again provided that they are compatible and the resulting refractive index of the vehicle is appropriately adjusted.

The components are blended together in appropriate quantities to give a vehicle with an appropriate $\eta_D$. Most preferably, the $\eta_D$ of the vehicle is virtually identical to that of the active antiperspirant particles. Even when the refractive indices are not identical, however, a substantially clear antiperspirant can be obtained. For example, where the active antiperspirant component is aluminum chlorohydrate ($\eta_D$ is about 1.51), a substantially clear antiperspirant is obtained if the liquid vehicle has an $\eta_D$ between about 1.50 and 1.52; and where the active antiperspirant component is aluminum chlorohydrate (or adduct) with additional associated water ($\eta_D$ is about 1.495), a substantially clear antiperspirant is obtained if the liquid vehicle has an $\eta_D$ between about 1.49 and 1.51. The term "match", as used herein, means the refractive indices are close enough such that an antiperspirant product is obtained that has a turbidity value not in excess of 800 FTU.

The gelling agent used in particular antiperspirant products is compatible with the other components, desirably forms a solution with other liquid components, and, in conjunction with other vehicle components, meets the $\eta_D$ requirements for a substantially clear antiperspirant. Examples of suitable gelling agents include polyethylene-vinyl acetate copolymers, polyethylene homopolymers and blends. Allied Corp's grade 6 and 6A homopolymers and 400 and 400A copolymers are preferred gelling agents. It will be apparent that other appropriate gelling agents with suitably matched refractive indices can be used. The amount of gelling agent in the solid antiperspirant product preferably is sufficient to cause the liquid vehicle to gel (i.e., become free-standing). In general, the solid antiperspirant product should include between about 2% and about 50% (more preferably between about 10% and about 35%, most preferably between about 15% and about 30%) of gelling agent. For liquid antiperspirant products, it may be desirable to use some gelling agent in the antiperspirant product for thickening, even though a sufficient quantity of gelling agent is not used to obtain a free-standing composition.

In accordance with a further aspect of the invention, care is taken in the blending of components to achieve optimum clarity of a gel antiperspirant product. In making a substantially clear essentially anhydrous antiperspirant product, a gelling agent is dissolved in the vehicle component at a temperature of less than the cloud point of the gelling agent; an active antiperspirant component (directly or in adduct form) is added to the gelling agent-vehicle component, the refractive index of the active antiperspirant component matching that of the gelling agent-vehicle component; and the mixture of the gelling agent-vehicle component and the active antiperspirant component is cooled to provide an antiperspirant product that has a relative turbidity of less than 400 FTU.

In preferred embodiments, the active antiperspirant component is aluminum chlorohydrate with a refractive index (depending on the amount of associated water) between about 1.46 and 1.53; and the refractive indices ($\eta_D$) of the active antiperspirant component and of the gelling agent-vehicle component are within about 0.02. The process may include the step of adding water to the aluminum salt in solid form to reduce its refractive index without significant dissolution of the solid aluminum salt.

In a particular process, an antiperspirant product that includes a polyethylene-vinyl acetate copolymer (AC-400) as a gelling agent is processed as follows: (1) the active antiperspirant component and the polyethylene-vinyl acetate copolymer are added to other vehicle components; (2) the mixture is heated to a temperature below 80° C. (preferably between 70° C. and 80° C.; and most preferably about 75° C.) to dissolve the copolymer; and the mixture is cooled.

Although the precise technical reason the above process provides an optimally clear solid antiperspirant product is undetermined, it is felt that keeping the highest processing temperature below the cloud point of the gelling agent (a polyethylene-vinyl acetate copolymer (such as Allied Corp. AC-400A, which has a $\eta_D$ of about 1.497) generally has a cloud point above 80° C., and a polyethylene homopolymer (such as Allied Corp. AC-6A, which has $\eta_D$ of about 1.51) generally has a cloud point above 95°-100° C.) provides the clearest antiperspirant product. Heating above the cloud point may cause a change in the structure of the gelling agent which may change the refractive index and result in a hazy antiperspirant product.

The following Examples 1-12 illustrate representative antiperspirant products and are given by way of illustration only and are not to be considered as being limiting. The amounts in the Examples and the claims are in weight percent.

The following Examples are made by combining and mechanically mixing all the liquid vehicle ingredients until homogeneous and refractive index is adjusted as necessary, for example to 1.5075 where dry aluminum chlorohydrate in adduct form is the antiperspirant product active; to 1.4955 where aluminum chlorohydrate in adduct form contains additional associated water is the antiperspirant product active; and to about 1.56 where aluminum-zirconium chlorohydrate is the antiperspirant product active. The active ingredient is then added, and the mixture is heated from room temperature to 60° C. over a period of about one-quarter hour. At 60° C., a gellant (e.g., a polyethylene-vinyl acetate copolymer) (if used) is added and the mixture is continued to be heated to about 75° C. (a temperature where the gellant has melted and the mixture appears to be homogeneous). The mixture is held at 75° C. for about ten minutes and then deaerated as appropriate and poured into molds.

EXAMPLE 1

| Ingredient | Percentage | |
|---|---|---|
| Octylmethoxy Cinnamate | 50.25 | |
| Isopropyl myristate | 17.25 | |
| Ethanol - 200 proof | 2.50 | |
| Aluminum chlorohydrate | 10.00 | |
| Polyethylene/Vinyl Acetate Copolymer | 20.00 | |

The resulting composition of Example 1 was a solid and had a measured turbidity of 148 FTU.

EXAMPLE 2

| Ingredient | Percentage | |
|---|---|---|
| Octylmethoxy Cinnamate | 43.50 | |
| Isopropyl myristate | 14.50 | |
| Ethanol - 200 proof | 2.50 | |
| Aluminum Chlorohydrate | 30.00 | adduct form |
| Oleth-10 | 7.50 | |
| Polyethylene/Vinyl Acetate Copolymer | 2.00 | |

The resulting composition of Example 2 was a viscous fluid and had a measured turbidity of 45 FTU.

EXAMPLE 3

| Ingredient | Percentage | |
|---|---|---|
| Octylmethoxy Cinnamate | 39.75 | |
| Isopropyl myristate | 12.75 | |
| Ethanol - 200 proof | 2.50 | |
| Aluminum Chlorohydrate | 20.00 | adduct form |
| Oleth-10 | 5.0 | |
| Polyethylene/Vinyl Acetate Copolymer | 20.00 | |

The resulting composition of Example 3 was a solid and had a measured turbidity of 87 FTU.

EXAMPLE 4

| Ingredient | Percentage | |
|---|---|---|
| Octylmethoxy Cinnamate | 34.33 | |
| Isopropyl myristate | 10.67 | |
| Ethanol - 200 proof | 2.50 | |
| Aluminum Chlorohydrate | 30.00 | adduct form |
| Oleth-10 | 7.50 | |
| Polyethylene/Vinyl Acetate Copolymer | 15.00 | |

The resulting composition of Example 4 was a solid and had a turbidity of 102 FTU.

EXAMPLE 5

| Ingredient | Percentage | |
|---|---|---|
| Octylmethoxy Cinnamate | 24.50 | |
| Finsolv TN | 18.00 | |
| Ethanol - 200 proof | 2.50 | |
| Aluminum Chlorohydrate | 30.00 | adduct form |
| Procetyl AWS | 10.00 | |
| Polyethylene/Vinyl Acetate Copolymer | 15.00 | |

The resulting composition of Example 5 was a solid and had a turbidity of 127 FTU.

EXAMPLE 6

| Ingredient | Percentage | |
|---|---|---|
| Octylmethoxy Cinnamate | 13.53 | |
| Finsolv TN | 44.47 | |
| Water (added to the adduct) | 2.00 | |
| Aluminum Chlorohydrate | 15.00 | adduct form |
| Procetyl AWS | 5.00 | |
| Polyethylene/Vinyl Acetate Copolymer | 20.00 | |

The resulting composition of Example 6 was a substantially clear solid, had a refractive index of 1.4949, and had a turbidity of 234 FTU.

EXAMPLE 7

| Ingredient | Percentage | |
|---|---|---|
| Octylmethoxy Cinnamate | 27.50 | |
| Finsolv TN | 20.00 | |
| Ethanol - 200 proof | 2.50 | |
| Aluminum Chlorohydrate | 30.00 | adduct form |
| Procetyl AWS | 5.00 | |
| Polyethylene/Vinyl Acetate Copolymer | 15.00 | |

The resulting composition of Example 7 was a solid and had a turbidity of 100 FTU.

EXAMPLE 8

| Ingredient | Percentage | |
|---|---|---|
| Isoamyl Methoxy Cinnamate | 30.89 | |
| Isopropyl Myristate | 11.61 | |
| Ethanol - 200 proof | 2.50 | |
| Isoeicosane | 5.00 | |
| Aluminum Chlorohydrate | 20.00 | adduct form |
| Oleth-10 | 5.00 | |
| Stearyl Alcohol | 2.00 | |
| Polyethylene/Vinyl Acetate Copolymer | 23.00 | |

The resulting composition of Example 8 was a solid and had a turbidity of 121 FTU.

EXAMPLE 9

| Ingredient | Percentage | |
|---|---|---|
| Isoamyl Methoxy Cinnamate | 34.14 | |
| Isopropyl Myristate | 8.36 | |
| Ethanol - 200 proof | 2.50 | |
| Polyphenylmethylsiloxane (DC556) | 5.00 | |
| Aluminum Chlorohydrate | 20.00 | adduct form |
| Oleth-10 | 5.00 | |
| Stearyl Alcohol | 2.00 | |
| Polyethylene/Vinyl Acetate Copolymer (AC400A) | 23.00 | |

The resulting composition of Example 9 was a solid and had a turbidity of 156 FTU.

EXAMPLE 10

| Ingredient | Percentage | |
|---|---|---|
| Octylmethoxy Cinnamate | 33.6 | |
| Isopropyl Myristate | 10.4 | |
| Ethanol - 200 proof | 2.50 | |
| Rehydrol II | 30.00 | adduct form |
| Oleth-10 | 7.50 | |

-continued

| Ingredient | Percentage |
|---|---|
| Polyethylene/Vinyl Acetate Copolymer (AC 400A) | 16.00 |

The resulting composition of Example 10 was a solid and had a turbidity of 56 FTU.

EXAMPLE 11

| Ingredient | Percentage |
|---|---|
| Isoamyl Methoxy Cinnamate | 72.3 |
| Cinnamic Aldehyde | 7.7 |
| Aluminum Zirconium Chlorohydrate | 20.00 |

The resulting composition of Example 11 was a liquid and had a turbidity of 450 FTU.

EXAMPLE 12

| Ingredient | Percentage |
|---|---|
| Octylmethoxy Cinnamate | 43.10 |
| Isopropyl Myristate | 14.80 |
| Alcohol SD-40 | 2.10 |
| Aluminum Chlorohydrate | 20.00 |
| Polyethylene/Vinyl Acetate Copolymer AC400A | 20.00 |

The resulting composition of Example 12 was a solid and had a turbidity of 290 FTU.

While particular embodiments of the invention has been shown and described, various modifications will be apparent to those skilled in the art, and therefore it is not intended that the invention be limited to the disclosed embodiments or to details therof, and departures may be made therefrom within the spirit and scope of the invention.

What is claimed is:

1. A substantially clear essentially anhydrous antiperspirant composition comprising an antiperspirant effective amount of an aluminum chlorohydrate or aluminum-zirconium chlorohydrate antiperspirant salt in solid particulate form suspended in an essentially anhydrous vehicle, said antiperspirant salt being substantially free of opacifying contaminants and the refractive indices of said antiperspirant salt and said vehicle being between about 1.46 and about 1.56 and matching to within about 0.02 such that the relative turbidity of said antiperspirant composition is less than 800 FTU.

2. The antiperspirant composition of claim 1 wherein the refractive indices of said antiperspirant salt and said vehicle are matched such that the relative turbidity of said antiperspirant composition is less than 400 FTU.

3. The antiperspirant composition of claim 1 wherein said vehicle includes a gelling agent which has a refractive index between about 1.45 and about 1.53.

4. The antiperspirant composition of claim 3 wherein said antiperspirant composition includes between about 2% and about 50% of said gelling agent.

5. The antiperspirant composition of claim 4 wherein said gelling agent is a polyethylene homopolymer.

6. The antiperspirant composition of claim 4 wherein said gelling agent is a polyethylene-vinyl acetate copolymer.

7. The antiperspirant composition of claim 3 wherein said gelling agent is present in sufficient quantity to cause said composition to be a free-standing solid.

8. The antiperspirant composition of claim 7 wherein said antiperspirant composition includes between about 15% and about 30% of said gelling agent.

9. The antiperspirant composition of claim 8 wherein said vehicle includes an effective amount of a surfactant to impart washability to said antiperspirant composition.

10. The antiperspirant composition of claim 9 wherein said antiperspirant composition includes from about 10% to about 30% of said antiperspirant salt.

11. A substantially clear, essentially anhydrous, solid antiperspirant composition comprising an essentially anhydrous vehicle, said vehicle including a gelling agent in sufficient quantity to cause said composition to be a free-standing solid, and about 10% to about 30% by weight of an aluminum chlorohydrate or aluminum-zirconium chlorohydrate antiperspirant salt in solid particulate form suspended in said vehicle, said antiperspirant salt being substantially free of opacifying contaminants, and said antiperspirant salt and said vehicle each having a refractive index between about 1.46 and about 1.56 and matching to within about 0.02 such that the relative turbidity of said antiperspirant composition is less than 400 FTU.

12. The antiperspirant composition of claim 11 wherein said gelling agent has a refractive index between about 1.45 and 1.53.

13. The antiperspirant composition of claim 12 wherein said composition includes between about 15% and about 30% of said gelling agent.

14. A process for making a substantially clear essentially anhydrous antiperspirant composition comprising the steps of providing an aluminum chlorohydrate or aluminum-zirconium chlorohydrate antiperspirant salt in solid particulate form, said antiperspirant salt being substantially free of opacifying contaminants and having a refractive index between about 1.46 and about 1.56, providing an essentially anhydrous vehicle with a refractive index that matches the refractive index of said antiperspirant salt to within about 0.02 such that the relative turbidity of the resulting antiperspirant composition is less than 800 FTU, and suspending an antiperspirant effective amount of said antiperspirant salt in said vehicle.

15. The process of claim 14 wherein the refractive indices of said antiperspirant salt and said vehicle are matched such that the relative turbidity of the resulting antiperspirant composition is less than 400 FTU.

16. The process of claim 14 wherein said vehicle includes a gelling agent which has been dissolved therein at a temperature below the cloud point of said gelling agent so that the resulting antiperspirant composition is a free-standing solid.

17. The process of claim 16 wherein said antiperspirant composition includes between about 10% and about 35% of said gelling agent, and said gelling agent has a refractive index between about 1.45 and about 1.53.

18. The process of claim 14 wherein said antiperspirant salt is obtained by the steps of providing a solution of said antiperspirant salt in water and/or ethanol and evaporating said solution at a temperature below about 50° C. to provide said antiperspirant salt in solid form that is substantially free of opacifying contaminants.

19. The process of claim 18 wherein said solution further contains a surfactant, and said evaporating step provides an adduct of said antiperspirant salt with said surfactant.

20. The process of claim 19 wherein said surfactant is selected from the group consisting of Oleth-10 and PPG-5-Ceteth-20.

21. The process of claim 18 further including the step of adding water to said antiperspirant salt in solid form to reduce its refractive index without significant dissolution of said solid antiperspirant salt.

22. The process of claim 14 further comprising the steps of dissolving a polyethylene-vinyl acetate copolymer in said vehicle at a temperature of less than about 80° C., suspending said antiperspirant salt in said copolymer-vehicle solution, and cooling the mixture to provide a solid antiperspirant composition.

23. A process for making a substantially clear, essentially anhydrous, solid antiperspirant composition comprising the steps of providing an aluminum chlorohydrate or aluminum-zirconium chlorohydrate antiperspirant salt in solid particulate form, said antiperspirant salt being substantially free of opacifying contaminants and having a refractive index between about 1.46 and about 1.56, providing an essentially anhydrous vehicle with a refractive index that matches the refractive index of said antiperspirant salt to within about 0.02 such that the relative turbidity of the resulting antiperspirant composition is less than 400 FTU, dissolving a gelling agent in said vehicle at a temperature below the cloud point of said gelling agent, said gelling agent having a refractive index between about 1.45 and about 1.53 and being present in sufficient quantity to cause said composition to be a free-standing solid, suspending an antiperspirant effective amount of said antiperspirant salt in said vehicle, and cooling the mixture to provide a solid antiperspirant composition.

24. The process of claim 23 wherein said gelling agent is selected from polyethylene homopolymer and polyethylene-vinyl acetate copolymer.

* * * * *